(12) United States Patent
Aher et al.

(10) Patent No.: US 7,186,842 B2
(45) Date of Patent: Mar. 6, 2007

(54) POLYMORPH OF (1-BENZYL-4-[(5,6-DIMETHOXY-1-INDANONE)-2-Y1] METHYL PIPERIDINE HYDROCHLORIDE (DONEPEZIL HYDROCHLORIDE) AND A PROCESS FOR PRODUCING THEREOF

(75) Inventors: Umesh P. Aher, Kalyan (IN); Venkatasubramanian R. Tarur, Mumbai (IN); Dhananjay Govind Sathe, Thane (IN); Avinash Venkataraman Naidu, Dombivli (IN); Kamlesh Digambar Sawant, Mumbai (IN)

(73) Assignee: USV, Ltd., Mumbai (IN)

( * ) Notice: Subject to any disclaimer, the term of this patent is extended or adjusted under 35 U.S.C. 154(b) by 0 days.

(21) Appl. No.: 11/145,202

(22) Filed: Jun. 3, 2005

(65) Prior Publication Data

US 2005/0272775 A1   Dec. 8, 2005

Related U.S. Application Data

(63) Continuation-in-part of application No. 11/072,169, filed on Mar. 4, 2005, and a continuation-in-part of application No. 10/879,816, filed on Jun. 29, 2004, and a continuation-in-part of application No. 10/714,724, filed on Nov. 17, 2003, now Pat. No. 6,953,856, and a continuation-in-part of application No. 10/365,717, filed on Feb. 12, 2003, now Pat. No. 6,649,765.

(30) Foreign Application Priority Data

Jul. 28, 2004   (IN)  .................... PCT/IN04/00227

(51) Int. Cl.
   *C07D 211/32*   (2006.01)
   *A61K 31/445*   (2006.01)
(52) U.S. Cl. ..................................... 546/206; 514/319
(58) Field of Classification Search ............... 514/319; 546/206
   See application file for complete search history.

(56) References Cited

U.S. PATENT DOCUMENTS

| 4,895,841 A | 1/1990 | Sugimoto |
| 5,985,864 A * | 11/1999 | Imai et al. .................. 514/321 |
| 6,734,195 B2 | 5/2004 | Weisman |

FOREIGN PATENT DOCUMENTS

| EP | 1 323 712 A1 | 7/2003 |
| WO | WO 97/46527 | 12/1997 |
| WO | WO 2004/092137 | 10/2004 |

OTHER PUBLICATIONS

Usuelli, A, International Search Report (PCT/IN2004/00027), Int'l filing date Jul. 28, 2004, Apr. 13, 2005, European Patent Office, Munich, Germany.

* cited by examiner

*Primary Examiner*—Charanjit S. Aulakh
(74) *Attorney, Agent, or Firm*—Pharmaceutical Patent Attys, LLC

(57) ABSTRACT

The present invention discloses a novel, stable polymorph of 1-benzyl-4-[(5,6-dimethoxy-1-indanone)-2-yl] methyl piperidine hydrochloride commonly known as Donepezil hydrochloride. Further the present invention discloses a process for producing Donepezil HCl amorphous and its polymorph Form (VI).

9 Claims, 2 Drawing Sheets

POLYMORPH OF (1-BENZYL-4-[(5,6-DIMETHOXY-1-INDANONE)-2-Y1] METHYL PIPERIDINE HYDROCHLORIDE (DONEPEZIL HYDROCHLORIDE) AND A PROCESS FOR PRODUCING THEREOF

CROSS REFERENCE TO RELATED APPLICATIONS

This application is continuation-in-part of U.S. application Ser. No. 10/365,717 filed Feb. 12, 2003 now U.S. Pat. No. 6,649,765; Ser. No. 10/714,724, filed 17 Nov. 2003 now U.S. Pat No.6,953,856; Ser. No. 10/879,816, Filed 29 Jun. 2004; and Ser. No. 11/072,169, filed 4 Mar.2005, each incorporated herein by reference. This application claims priority from PCT/IN04/00227, filed 28 Jul. 2004, incorporated herein by reference.

TECHNICAL FIELD

The present invention relates to a novel, stable polymorph of 1-benzyl-4-[(5,6-dimethoxy-1-indanone)-2-yl] methyl piperidine hydrochloride commonly known as Donepezil hydrochloride. Further the present invention relates to a process for producing Donepezil HCl amorphous and it's polymorph Form (VI).

BACKGROUND

Donepezil hydrochloride (I) has excellent action as a prophylactic and a therapeutic agent for senile dementia, and in particular as a prophylactic and therapeutic agent for Alzheimer's disease and an industrial process for producing the same, has been reported.

The process for the preparation of 1-benzyl-4-[(5,6-dimethoxy-1-indanone)-2-yl] methyl piperidine has been described in JP A-64-79151 (U.S. Pat. No. 4,895,841, EP 296560).

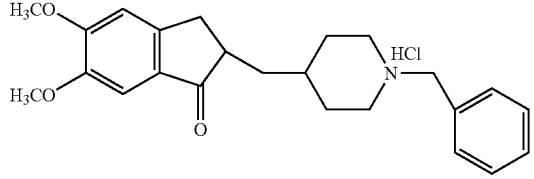

(I)

Japanese patent application, publication No. A-100-53576 (WO 9746527) discloses certain forms (I, II, III, IV & V) of Donepezil hydrochloride, 1-benzyl-4-[(5,6-dimethoxy-1-indanone)-2-yl] methyl piperidine hydrochloride. This patent also discloses an amorphous form of Donepezil hydrochloride, which is reported to be chemically unstable on storage.

U.S. Pat. No. 6,734,195 claims a chemically stable amorphous form of Donepezil hydrochloride and its use in formulation.

The U.S. Pat. No. 6,734,195 however has not reported any polymorphic stability of amorphous form. However the above JP patent A-100-53576 (WO 9746527) reports conversion of amorphous form to crystalline form (IV) when exposed to more than 90% relative humidity at room temperature.

SUMMARY

The present invention describes a novel, stable polymorph form (VI) of 1-benzyl-4-[(5,6-dimethoxy-1-indanone)-2-yl] methyl piperidine, hydrochloride.

The said polymorph form (VI) is characterized by powder X-ray diffraction patterns shown in FIG. 1. Further the said polymorph is characterized by IR recorded in KBr as shown in FIG. 2.

Further the present invention describes a process for making Donepezil hydrochloride amorphous from Donepezil oxalate wherein the said process comprises dissolving the said Donepezil oxalate in water in the temperature range of 40 to 60° C., preferably 50° C.; basifying the solution of said Donepezil oxalate with base to convert it into Donepezil base; extracting the said Donepezil base in a solvent; acidifying the said Donepezil base with inorganic acid, preferably hydrochloric acid to obtain the said Donepezil HCl and spray drying the said Donepezil HCl solution in water to obtain Donepezil HCl amorphous form.

Further the present invention describes a process for making Donepezil hydrochloride polymorph form (VI) from Donepezil hydrochloride amorphous at room temperature at relative humidity.

A pharmaceutical composition comprising a therapeutically effective amount of the said Donepezil HCl amorphous or its polymorph form (VI) is also envisaged as part of this invention.

A method of treating senile dementia of Alzheimer's disease, the method comprising administering to a warm blooded animal an effective amount of a product-by-process composition of matter comprising the said Donepezil HCl amorphous or its polymorphic form (VI) is also envisaged as part of this invention.

DETAILED DESCRIPTION

Surprisingly the amorphous form of Donepezil hydrochloride when prepared in our laboratory as reported in the JP A-100-53576 (WO 9746527), was found to undergo changes in the polymorphic form, when the amorphous form was kept at room temperature and a relative humidity of around 70%. This form was quite different than form (IV) reported in JP A-10-53576.

Thus we describe compound (I) as a novel polymorphic form of hydrochloride salt. The novel salt can be prepared by an efficient, economic and reproducible process and is particularly suited to large-scale preparation. The hydrochloride salt is therefore surprisingly amenable to large scale pharmaceutical processing and formulation.

The present invention specifically relates to the novel polymorphic form of Donepezil hydrochloride, which is characterized by powder X-ray diffraction and/or infrared absorption peaks recorded in potassium bromide.

The novel polymorphic form of compound (I) is hereafter referred as Donepezil hydrochloride form (VI).

The Donepezil hydrochloride form (VI) has specific melting characteristics. It melts in the range of 70 to 90° C., resolidifies in the range of 130 to 150° C. and remelts in the range of 210 to 230° C.

The present invention encompasses the Donepezil hydrochloride form (VI) isolated in a purified form.

Also, the invention provides Donepezil hydrochloride form (VI) in a pharmaceutically acceptable form, especially in bulk form, such form having good flow properties, especially good bulk flow properties.

The present invention uses Donepezil oxalate (reported in our earlier U.S. application Ser. No. 10/879,816 and herein incorporated by reference) which is prepared by treating 1-benzyl-4-[(5,6-dimethoxy-1-indanone)-2-yl] methyl piperidine compound (I) (Process for the Compound I is reported in our patent U.S. Pat. No. 6,649,765, herein incorporated as reference) with oxalic acid in suitable solvent.

The concentration of compound (I) is preferably in the range of from 3 to 25% weight/volume, more preferably in the range of from 5 to 20%. The concentration of oxalic acid solution is preferably in the range of from 3 to 50% weight/volume.

The reaction is usually carried out at ambient temperature or at an elevated temperature, although any convenient temperature that provides the required product may be employed. The temperature is in the range of 20–120° C., preferably 40° C. to 90° C., more preferably 70° C.

The suitable solvent is an alkanol, for example propan-2-ol, or a ketone, such as acetone, an ester, such as ethyl acetate.

The invention provides a novel process for the preparation of the Donepezil hydrochloride amorphous form, which comprises the following steps:

Donepezil oxalate is dissolved in water and basified. Donepezil base thus obtained, is extracted in a suitable solvent and acidified with aqueous hydrochloric acid. The solvent is evaporated and aqueous acidic solution of Donepezil hydrochloride is lyophilized to obtain Donepezil hydrochloride amorphous form.

The bases used are inorganic bases such as ammonia, sodium hydroxide, potassium hydroxide, sodium carbonate, sodium bicarbonate, preferably ammonia.

A suitable solvent is an organic solvent, such as toluene, ethyl acetate, a halogenated hydrocarbon such as dichloromethane, chloroform, preferably dichloromethane.

The concentration of Donepezil oxalate solution in water is preferably in the range of from 5 to 25% weight/volume, more preferably in the range of from 5 to 15%.

The dissolution of Donepezil oxalate in water is usually carried out at ambient temperature or at an elevated temperature, although any convenient temperature that provides the required product may be employed. The temperature is in the range of 20–80° C., preferably 25° C. to 50° C., more preferably 35° C.

Lyophilization is usually carried out in the temperature range of −20 to −80° C., preferably 5° C. to −50° C., more preferably −35° C.

The invention also provides a process for preparing Donepezil hydrochloride amorphous by spray drying Donepezil hydrochloride in water.

Spray drying is carried out in the temperature range of 80–120° C., preferably 90 to 110° C., more preferably 100° C.

The invention also provides a process for the preparation of the Donepezil hydrochloride form (VI), in which Donepezil hydrochloride amorphous is obtained by lyophilization or spray drying and kept at room temperature under humid atmosphere.

The room temperature is in the range of 25 to 35° C., preferably 29 to 31° C.

The relative humidity is in the range of 60 to 80%, preferably 65 to 75%.

X-ray powder diffraction pattern has been obtained on D 8-Advance, Bruker AXE, Germany, diffractometer equipped with scintillation detector using Copper Ka (λ=1.5406 Å) radiation with scanning range between 2–50 θ (theta) at scanning speed of 2°/min.

Detailed process for preparing the Donepezil hydrochloride form (VI) is given below, Donepezil base is prepared by a process as described in U.S. Pat. No. 6,649,765 B1 and is incorporated here as a reference. Thereafter the base is converted to the novel form (VI) of Donepezil hydrochloride as mentioned below:

1. Donepezil oxalate, obtained by treatment of ethyl acetate solution of Donepezil free base with a solution of oxalic acid in acetone is filtered and dried.
2. Donepezil oxalate is further purified in an organic solvent such as methanol.
3. Pure Donepezil oxalate is dissolved in water and basified with a base, such as sodium hydroxide to liberate Donepezil free base.
4. The Donepezil free base is extracted in dichloromethane.
5. Dichloromethane layer containing Donepezil free base is stirred with aqueous hydrochloric acid to form Donepezil hydrochloride.
6. Dichloromethane is evaporated to leave an aqueous solution of Donepezil hydrochloride.
7. The aqueous solution of Donepezil hydrochloride is lyophilized to form Donepezil hydrochloride amorphous.
8. The aqueous solution of Donepezil hydrochloride is spray dried to form Donepezil hydrochloride amorphous.
9. The Donepezil hydrochloride amorphous is exposed to humidity to form polymorph (VI).

Donepezil Hydrochloride Form (VI)

Peaks in the powder x-ray diffraction pattern are:

| Sr. No | Diffraction Angle (2 θ°) | Intensity % (I/Io) |
| --- | --- | --- |
| 1. | 6.026 | 21.2 |
| 2. | 9.630 | 19.6 |
| 3. | 10.183 | 48.8 |
| 4. | 11.043 | 21.6 |
| 5. | 11.657 | 70.5 |
| 6. | 12.065 | 18.0 |
| 7. | 12.741 | 75.1 |
| 8. | 13.186 | 14.4 |
| 9. | 13.769 | 27.7 |
| 10. | 14.390 | 35.9 |
| 11. | 16.194 | 18.1 |
| 12. | 17.510 | 53.7 |
| 13. | 18.140 | 19.8 |
| 14. | 19.289 | 18.7 |
| 15. | 19.799 | 24.0 |
| 16. | 20.381 | 91.4 |
| 17. | 20.720 | 61.3 |
| 18. | 21.400 | 100.0 |
| 19. | 21.841 | 62.1 |
| 20. | 22.944 | 46.6 |
| 21. | 24.649 | 54.0 |
| 22. | 25.433 | 40.4 |
| 23. | 26.203 | 17.1 |
| 24. | 27.011 | 14.0 |
| 25. | 28.309 | 25.6 |
| 26. | 31.586 | 14.2 |
| 27. | 32.516 | 21.4 |
| 28. | 35.633 | 11.6 |
| 29. | 40.696 | 12.5 |

Wave numbers ($cm^{-1}$) of infrared absorption spectra recorded in potassium bromide are: 443.6, 451.3, 464.8, 498.6, 518.8, 534.2, 549.3, 59.3, 605.6, 630, 651.9, 673, 707.8, 759.9, 785, 806.2, 848.6, 862.1, 891.1, 920, 947, 970.1, 979.8, 1010.6, 1037.6, 1064.6, 1085.9, 1116.7, 1157.2, 1193.9, 1224.7, 1265.2, 1317.3, 1363.6, 1429.2, 1454.2, 1469.7, 1468.6, 1589.2, 1604.7, 1629.7, 1691.5, 1913.3, 1992.3, 2061.8, 2248.8, 2345.3, 2542, 2561.3, 2588.3, 2636.5, 2669.3, 2696.3, 2721.4, 2835.2, 2873.7, 2925.8, 3031.9, 3255.6, 3355.9, 3367.5, 3517.9, 3548.8

Figure 1:
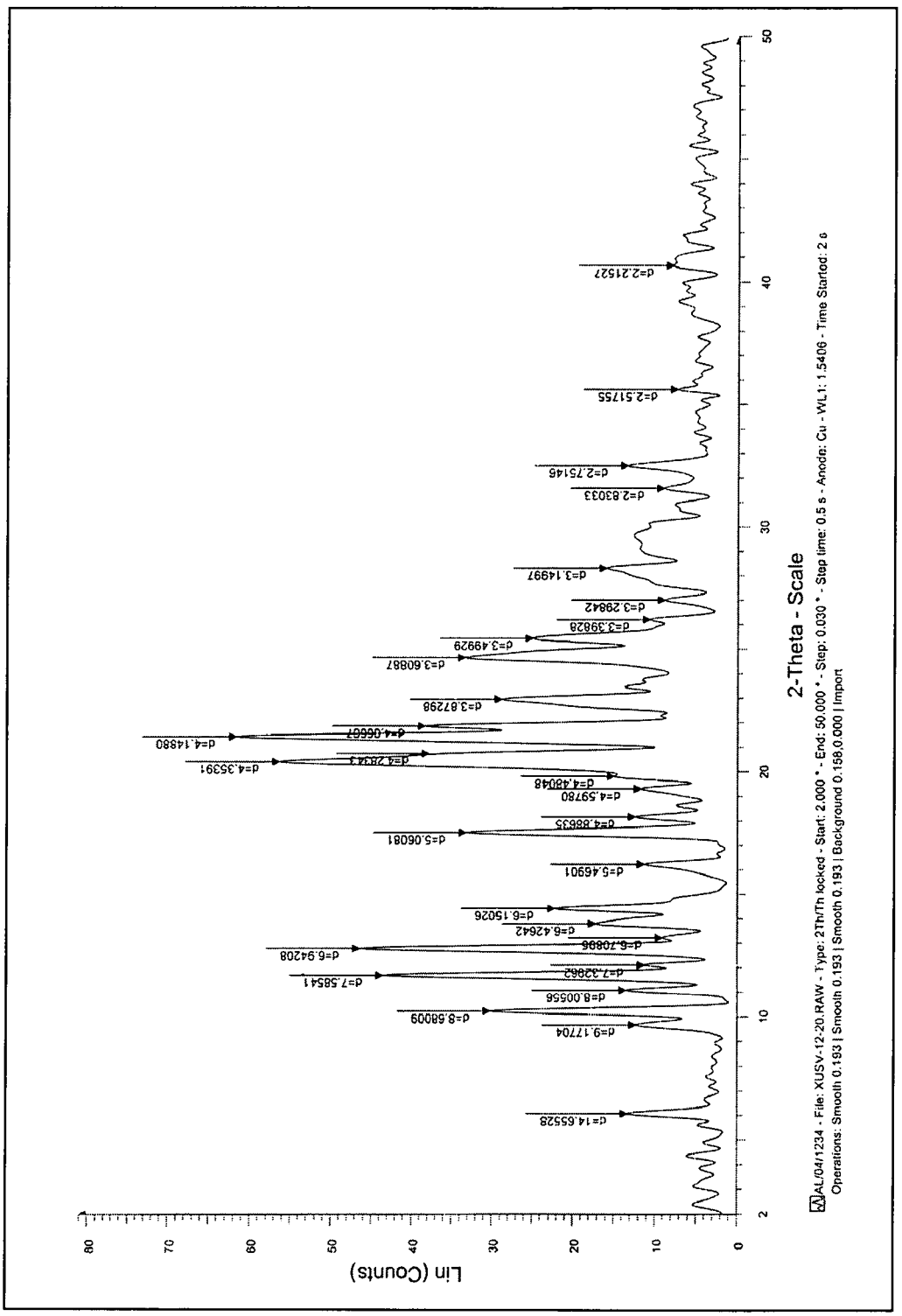
FIG. 1 shows a powder X-ray diffraction pattern for Donepezil hydrochloride form (VI)
Figure 2:
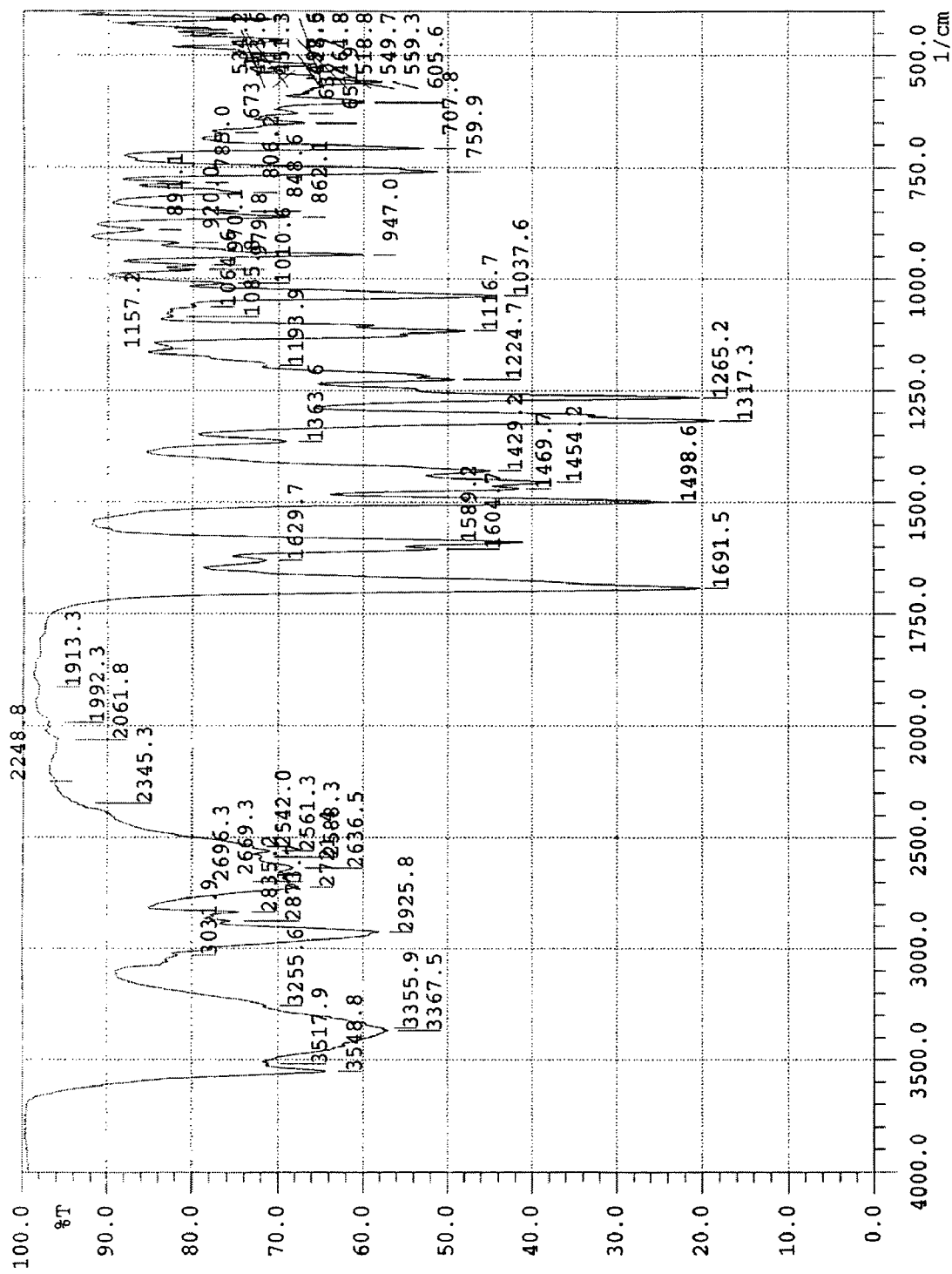
FIG. 2 shows an infrared absorption spectrum for Donepezil hydrochloride form (VI).

Donepezil hydrochloride form (VI):

Peaks in powder X-ray diffraction pattern (See FIG. 1):

Peaks in infrared absorption spectrum recorded in potassium bromide (See FIG. 2):

The designations of x-ray diffraction angles, x-ray intensities and infrared ("IR") wave values are approximate; the numerical values here disclosed are therefore intended to encompass a range of approximately ±0.3 about each stated value. Thus, for example, the term "IR values . . . as follows; 443.6, 451.3, 464.8" is intended to encompass IR values of a range of from 443.3 to 443.9; and a range of from 451.0 to 451.6; and a range of from 464.5 to 465.1. Similarly, claim terms incorporating parameters illustrated by the Figures do not require exact equality in physical characteristics; a variation of approximately ±0.3 about each value along the parameters shown in each Figure is to be expected.

EXAMPLES

The present invention will now be described in more detail with reference to the following examples. It is needless to say that the technical scope of the present invention is not limited to these examples.

Example 1

To Donepezil base (obtained after benzylation which is reported in our patent U.S. Pat. No. 6,649,765, herein incorporated as reference) (10 gms.) in ethyl acetate (200 ml) was added oxalic acid (5 gms dissolved in 100 ml acetone) slowly with stirring. After addition, the reaction mass was concentrated in vacuum. The solid separated was filtered, washed with acetone and dried at 60° C. to afford the title compound with a yield of 12 gms (90.2%) and melting point of 176–77° C.

Example 2

Donepezil oxalate 5 gms was dissolved in methanol 25 ml under heating at 50° C. Stirring was continued for 1 hour with gradual cooling. Stirring was further continued for 1 hour at room temperature. Filtration of the crystals and drying at 60° C. afforded the title compound with a yield of 4.0 gms (80%) and melting point of 177–78° C.

Example 3

Donepezil oxalate (purified, example 2), 5 gms, was dissolved in water 50 ml under heating at 50° C. Stirring was continued for 1 hour with gradual cooling. At room temperature, dichloromethane 50 ml was added and stirred for 10 mins. Liquid Ammonia 5 ml was added slowly with stirring. The dichloromethane layer was separated and 50 ml water was added to it. Analytical grade concentrated hydrochloric acid 1.5 ml was slowly added and stirred for 10 mins. Dichloromethane was distilled off under vacuum at 45° C. to obtain Donepezil hydrochloride in water, which was kept for lyophilyzation for 24 hours at −35° C. to give Donepezil hydrochloride amorphous with a yield of 3.9 gms (95%).

Example 4

Donepezil hydrochloride in water (prepared as given in example 3), which was spray dried at 100° C., to give Donepezil hydrochloride amorphous with a yield of 3.4 gms (82.9%).

Example 5

Donepezil hydrochloride amorphous 5 gm was kept at room temperature at relative humidity 70–80% for 24 hours to give the Donepezil hydrochloride form (VI) with a yield of 5.3 gms and melting point 215–218° C. Moisture content (KF 6.4%).

We claim:

1. 1-benzyl-4-[(5,6-dimethoxy-1-indanone)-2-yl] methyl piperdine hydrochloride having a powder X-ray diffraction peak selected from the group consisting of: 11.657; 12.065 and 14.390.

2. The compound claimed in claim 1, wherein the said compound is characterized by peaks at the diffraction angles (2 theta) in its powder X-ray diffraction pattern, as given below:

| Sr. No | Diffraction Angle (2 theta°) | Intensity % (I/Io) |
|---|---|---|
| 1. | 10.183 | 48.8 |
| 2. | 11.043 | 21.6 |
| 3. | 11.657 | 70.5 |
| 4. | 12.065 | 18.0 |
| 5. | 12.741 | 75.1 |
| 6. | 14.390 | 35.9 |
| 7. | 16.194 | 18.1 |
| 8. | 17.510 | 53.7 |
| 9. | 18.140 | 19.8 |
| 10. | 20.381 | 91.4 |
| 11. | 20.720 | 61.3 |
| 12. | 21.400 | 100.0 |
| 13. | 21.841 | 62.1 |
| 14. | 24.649 | 54.0 |
| 15. | 25.433 | 40.4. |

3. The compound claimed in claim 1, wherein the said compound is characterized by peaks at wave numbers in cm$^{-1}$ in IR recorded in KBr as given below: 651.9, 707.8, 759.9, 806.2, 848.6, 862.1, 947, 970.1, 979.8, 1037.6, 1116.7, 1224.7, 1265.2, 1317.3, 1363.6, 1454.2, 1469.7, 1468.6, 1589.2, 1604.7, 1629.7, 1691.5, 2561.3, 2588.3, 2636.5, 2669.3, 2721.4, 2835.2, 2873.7, 2925.8, 3255.6, 3355.9, 3367.5, 3517.9, 3548.8.

4. A process for making Donepezil hydrochloride amorphous from Donepezil oxalate comprising dissolving Donepezil oxalate in water in the temperature range of 40 to 60° C.; basifying the solution of said Donepezil oxalate with base to convert it into Donepezil base; extracting said Donepezil base in a solvent; acidifying said Donepezil base with hydrochloric acid to obtain the said Donepezil HCl; and spray drying the said Donepezil HCl solution to obtain Donepezil HCl amorphous form.

5. The process as claimed in claim 4 wherein the said base used is selected from the group consisting of: ammonia, sodium hydroxide, potassium hydroxide, sodium carbonate, and sodium bicarbonate.

6. The process as claimed in claim 4 wherein the said solvent is selected from the group consisting of: a hydrocarbon, an ester, a halogenated hydrocarbon, and chloroform.

7. The process as claimed in any one of claims 4, 5 or 6 wherein said Donepezil hydrochloride is spray dried in the temperature range of 80 to 120° C.

8. The compound of claim 1, having at least two powder X-ray diffraction peaks selected from the group consisting of: 11.657; 12.065 and 14.390.

9. The compound of claim 8, having powder X-ray diffraction peaks of 11.657 and 14.390.

* * * * *